United States Patent [19]
Villalta

[11] Patent Number: 5,370,633
[45] Date of Patent: Dec. 6, 1994

[54] ANATOMICAL VAGINAL TAMPON

[76] Inventor: Josue J. Villalta, 11923 Discovery Cir., Indianapolis, Ind. 46236

[21] Appl. No.: 127,799

[22] Filed: Sep. 28, 1993

Related U.S. Application Data

[63] Continuation-in-part of Ser. No. 724,843, Jul. 2, 1991, abandoned.

[51] Int. Cl.$^5$ .................. A61F 13/15; A61F 13/20
[52] U.S. Cl. .................. 604/385.1; 604/11; 604/13; 604/904; 128/830
[58] Field of Search .................. 604/358, 379–380, 604/385.1, 904, 11–13, 1; 128/830, 841, 839, 834

[56] References Cited

U.S. PATENT DOCUMENTS

| | | | |
|---|---|---|---|
| 2,141,026 | 12/1938 | Valle | 128/834 |
| 3,068,867 | 12/1962 | Bletzinger et al. | 604/904 |
| 3,128,762 | 4/1964 | Young | 128/834 |
| 3,196,873 | 7/1965 | Bletzinger et al. | |
| 3,322,123 | 5/1967 | Griswold et al. | 604/904 |
| 3,726,277 | 4/1973 | Hirschnaan | |
| 3,845,767 | 11/1974 | Friese et al. | |
| 4,286,594 | 9/1981 | Cunningham | |
| 4,291,696 | 9/1981 | Ring | |

FOREIGN PATENT DOCUMENTS

| | | | |
|---|---|---|---|
| 1204117 | 9/1970 | United Kingdom | |
| 2153686 | 8/1985 | United Kingdom | 128/830 |

*Primary Examiner*—Randall L. Green
*Assistant Examiner*—P. Zuttarelli
*Attorney, Agent, or Firm*—Woodard, Emhardt, Naughton, Moriarty & McNett

[57] ABSTRACT

An anatomically designed vaginal tampon. The main body of the tampon has an external configuration complimentary in shape to the vagina. The main body has a pair of side ridges connected to an intermediate wall forming an external configuration resembling a capital H. One end of the tampon includes an outwardly opening cavity to fittingly receive the uterine cervix limiting movement of the tampon. A thin walled sleeve may be loaded with the tampon and then inserted in the vagina. A plunger contacts the tampon while the sleeve is withdrawn.

12 Claims, 2 Drawing Sheets

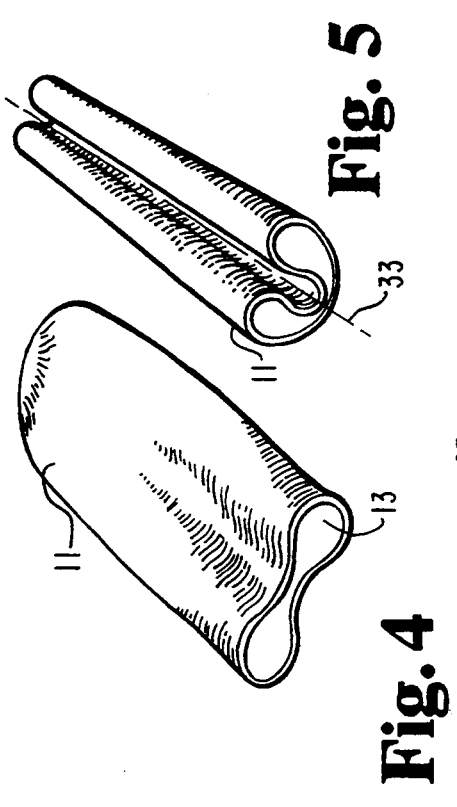
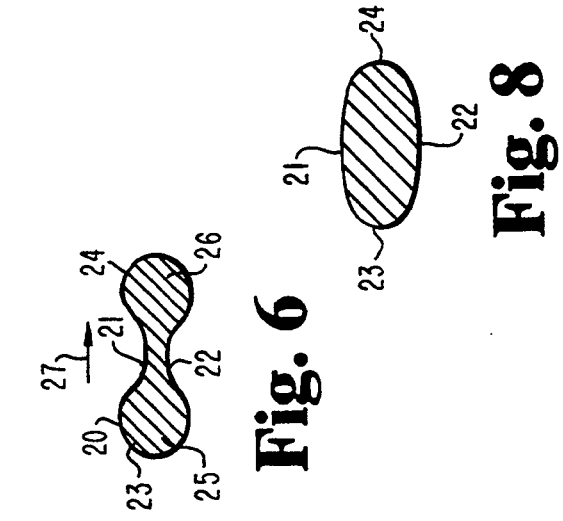
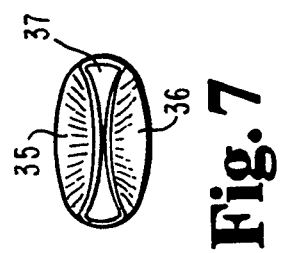
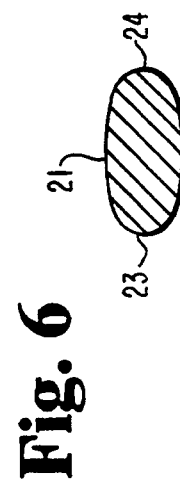
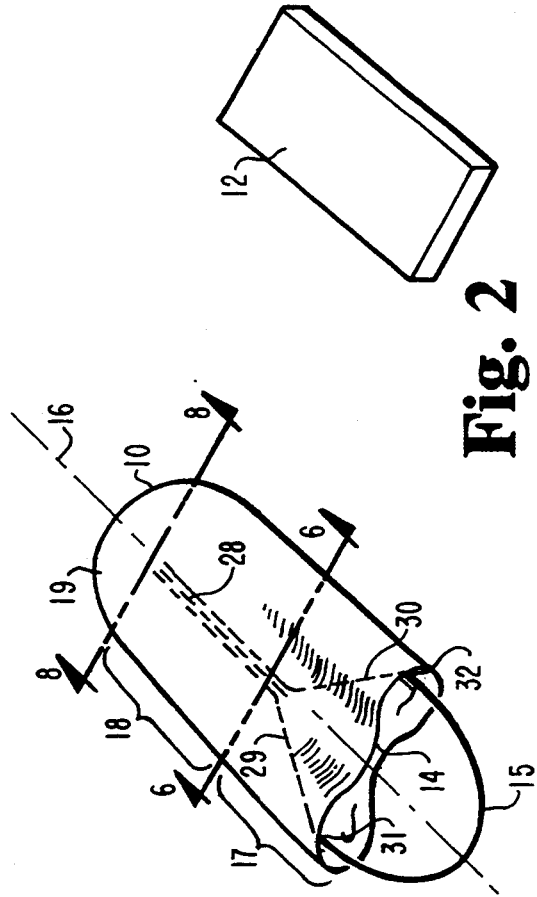
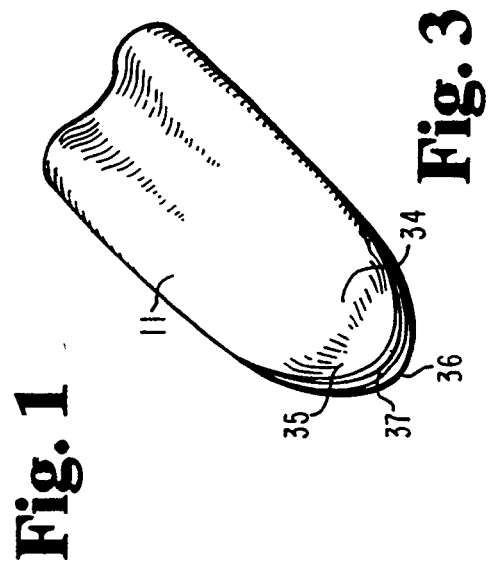

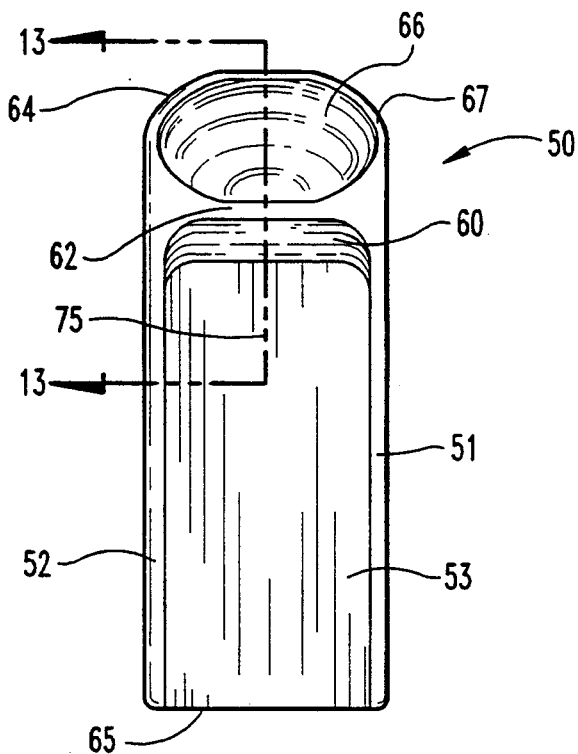
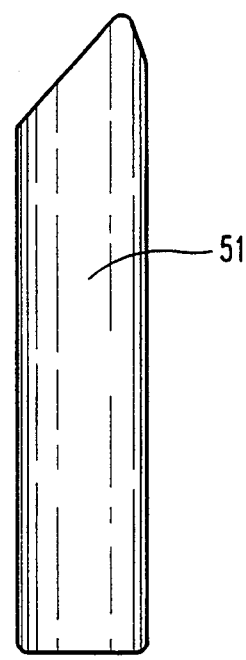
Fig. 9   Fig. 11
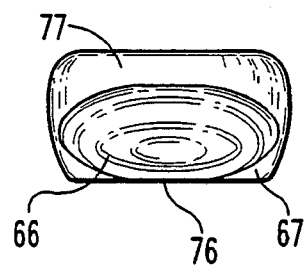
Fig. 12
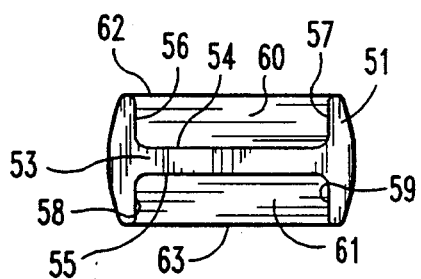
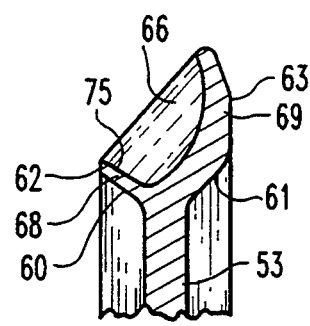
Fig. 10   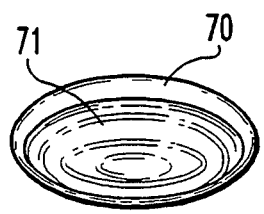   Fig. 13
Fig. 14

ANATOMICAL VAGINAL TAMPON

CROSS REFERENCE TO RELATED APPLICATION

This application is a continuation-in-part of my co-pending U.S. patent application Ser. No. 07/724,843, filed Jul. 2, 1991 now abandoned.

BACKGROUND OF THE INVENTION

1. Field of the Invention

This invention is in the field of tampons and applicators for use with vaginal menstrual flow or bleeding of any kind.

2. Description of the Prior Art

Vaginal tampons have been used for decades as feminine hygiene adjuvants with great degree of public acceptance. There are several designs that in essence vary the amount of material and size of the tampon. The tampons have been approved for human use, mass produced, commercially available and widely used by females throughout the world. The prior tampons consist of a rolled up piece of cotton/polyester material to which a fabric string has been attached typically by sewing. The rolled up material comes packaged in a cylindrical inserter, plastic or cardboard, that contains a small cylinder made of the same substance that is used as a plunger to push up the tampon. Once the tampon is inserted in the vagina the fabric string will hang out after the inserter is withdrawn and discarded.

Existing tampons have several disadvantages inherent in the design. First, the commercially available prior tampons essentially have the same length of two inches. Since the length of the vaginal canal is approximately four inches in the adult female, the existing available tampons may be inserted at different depths into the vaginal canal allowing for failure in absorbency, leakage, and expulsion.

A major disadvantage of the prior tampons is the external configuration or geometry of the tampon main body. The shape of the existing tampons is roughly cylindrical with variations in the amount of the cotton/polyester fiber. Typically, six to nine grams of the fiber is utilized and is accepted by the Association of Tampon Producers. The internal shape of the walls of the vaginal canals however, does not resemble a cylinder. The anterior and posterior walls are in contact forming in cross section a figure approximating capital H or a flattened transverse number 8. As a result, the existing tampons having a cylindrical shape allow the tampon to be placed at random on either side of the vaginal canal or worse transversely defeating its purpose of catching menstrual flow or bleeding.

The two prior disadvantages combine resulting in uncontrolled or random placement of the tampon. Since there is no relationship between the cylindrical tampon and the place of containment, the main purpose of optimal absorbency of uterine menstrual flow or bleeding is not achieved with the commercially available tampons. Users frequently complain of poor protection due to: a) overflow leakage wherein the amount of available cotton/polyester material absorbs only few milliliters of blood/menstrual flow, forcing the user to frequent changes of saturated tampons, and b) the uncertain placement of the tampon intra/vaginally allows for 1) menstrual flow/blood bypassing the tampon, 2) early expulsion, 3) external leakage of menstrual flow/blood when the hanging string is saturated, and 4) difficulty and inability to withdraw the tampon when the string has been pulled into the vaginal canal during insertion or when the tampon inadvertently has been placed transversely and high. This latter disadvantage and complication sets the ideal conditions for the production of Toxic Shock Syndrome since the inserted tampon is easily forgotten in place or becomes unreachable.

A representable sample of the prior devices include those disclosed in U.S. Pat. Nos. 4,286,594 issued to Cunningham; 3,845,767 issued to Friese et al; 3,726,277 issued to Hirschman; 3,196,873 issued Bletzinger et al; 4,291,696 issued to Ring; and in the British Patent Specification 1,204,117 issued to Ellis. The Cunningham device includes an applicator sleeve which is withdrawn as the tampon remains stationary. The Friese et al device includes a tampon having various geometric configurations. The Hirschman device includes a tampon with a circular configuration and a node extending therefrom. The Bletzinger et al device includes a tampon and applicator with the tampon being compressed into the applicator and then expanding when withdrawn. The Ring device includes a tampon applicator with distal leafs forming a tampon closure means' and the Ellis device includes a tampon of resilient material having end portions of uniform circular cross section and an intermediate portion of reduced cross section to allow the tampon to be flexed.

It is desired to prevent movement of the tampon once inserted. Thus, the preferred embodiment of the tampon disclosed herein includes a hollow distal end configured to fittingly receive the cervix of the uterus. Further, a pair of channels are formed on the opposite sides of the tampon to facilitate a conforming fit.

SUMMARY OF THE INVENTION

One embodiment of the present invention is an anatomical shaped vaginal tampon having a main body with length and a first end and a second end. A longitudinal axis extends between the ends centrally along the length of the main body. The main body is absorbent and operable to absorb menstrual flow with the main body having a pair of side ridges and a recessed intermediate wall extending therebetween. The first end of the main body when inserted first into a vagina will receive the cervix of the uterus and cooperatively with the intermediate wall and the side walls complimentary fit within the vagina limiting movement of the tampon.

It is an object of the present invention to provide a new and improved vaginal tampon designed to conformingly receive the uterine cervix.

A further object of the present invention is to provide a tampon having an external configuration complimentary in shape to a vagina.

An additional object of the present invention is to provide a tampon for filling up the vaginal cereal without user discomfort and provide optimal absorption of menstrual flow/blood.

A further object of the present invention is to provide an anatomically fit tampon which is accurately positioned.

Yet another object of the present invention is to provide a tampon having a withdrawal loop concealable between the vulvar folds preventing leakage of menstrual flow/blood and allowing for easy retrieval.

Related objects and advantages of the present invention will be apparent from the following description.

BRIEF DESCRIPTION OF THE DRAWING

It is understood that the following figures and their related descriptions are only given as examples to illustrate the invention and do not in any way constitute a limitation.

FIG. 1 is a perspective view of the tampon incorporating an alternate embodiment of my present invention.

FIG. 2 is a perspective view of the plunger or stop means to facilitate insertion of the tampon of FIG. 1.

FIG. 3 is a forward perspective view of the applicator sleeve utilized for insertion of the tampon of FIG. 1.

FIG. 4 is an aft perspective view of the sleeve of FIG. 3.

FIG. 5 is the same view as FIG. 4 only showing the sleeve in a folded condition.

PIG. 6 is a cross sectional view taken along the line 6—6 of FIG. 1 and viewed in the direction of the arrows.

FIG. 7 is a forward end view of the sleeve of FIG. 3.

FIG. 8 is a cross sectional view taken along the line 8—8 of FIG. 1 and viewed in the direction of the arrows.

FIG. 9 is a plan view of the preferred embodiment of the tampon incorporating my present invention.

FIG. 10 is bottom end view of the tampon of FIG. 9.

FIG. 11 is a side view of the tampon of FIG. 9.

FIG. 12 is a top end view of the tampon of FIG. 9.

FIG. 13 is a cross-sectional view taken along a line and viewed in the direction of arrows 13—13 of FIG. 9.

FIG. 14 is a the same view as FIG. 12 only showing an alternate shape of the distal end of the tampon.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawing, there is shown an alternate embodiment of a tampon 10 insertable within applicator sleeve 11 and then together insertable into the vagina. Once inserted, a plunger or stop means 12 is introduced into the open aft end 13 of sleeve 11 abutting against end 14 of tampon 10. Stop means 12 is then held stationary along with tampon 10 and sleeve 11 is withdrawn. Plunger or stop means 12 is then removed leaving tampon 10 within the vagina. A string loop 15 has opposite ends attached to the opposite sides of the main body of tampon 10 and may normally be concealed between the vulva folds (labia majora). In order to retrieve the tampon, the user reaches between the vulva folds and pulls on loop 15. The attached opposite ends of loop 15 will then bring together the opposite side end portions of the tampon facilitating the removal.

The shape or external configuration of tampon 10 is particularly critical and forms the basis of the present invention whereas the shape or external configuration of plunger 12 is not critical. Plunger 12 may taken a variety of shapes so long as one end of the plunger is abuttable through end 13 of sleeve 11 against the aft end 14 of the tampon. Thus, while the shape of plunger 12 is shown in the drawing as ruler shaped, it is understood that a sleeve shape, rod shape or other suitable shape is acceptable.

As discussed previously hereby, the transversal shape of the walls of the vaginal canal resembles a flat number 8. This anatomical configuration forces uterine and vaginal fluids to flow out following the lateral vaginal fornices or canals. The inner third walls of the vaginal canal do not follow this pattern but are separated by the presence of the uterine cervix in a semi-flat conical shape forming the vaginal vault. This particular anatomical configuration allows for pooling of uterine/cervical fluids at this anatomical location. The present invention has been designed following these vaginal anatomical configurations and fluid physiology in order to optimize its absorbency and therefore its protective advantages. As a result, the tampon has a varying external configuration along its longitudinal axis. The inner third of the tampon main body is not flat but assumes an oval shape allowing for better contact with menses/blood pooled at the vaginal vault. The remaining two thirds of the tampon main body extending along the longitudinal axis has the previously discussed flattened figure 8 configuration.

The longitudinal axis 16 extends centrally through the tampon main body with the tampon being generally symmetrical on opposite sides of the axis. The aft end portion 17 and medial portion 18 of the tampon has the same general external configuration. More specifically, the external surface 20 of the tampon includes an upper surface 21 and lower surface 22 extending between a pair of lateral or side surfaces 23 and 24. Surfaces 23 and 24 each form opposite sides of the main body of the tampon and extend through oppositely facing curves. That is, surface 23 opens to the right whereas surface 24 opens to the left as viewed in FIG. 6. The four surfaces form a generally flattened figure 8 shape which is complementary to the interior shape of the vagina. An alternate description of the configuration formed by surfaces 21-24 is that the lateral surfaces 23 and 24 each form opposite sides of the main body and extend through oppositely racing curves with the upper surface 21 and lower surface 22 being flattened and extending therebetween. Likewise, external surface 20 defines an elongated shape across the width of the main body in the direction of arrow 27 including opposite rounded sides extending lengthwise along axis 16 with the external surface being depressed at surfaces 21 and 22 to be complimentary in shape to the vagina. As shown in FIG. 1, the end 14 of the aft end portion 17 of the tampon has generally the same shape or external configuration as the medial portion 18 of the tampon as illustrated in FIG. 6.

The forward end portion 19 of the tampon does not have the external configuration as the aft end portion 17 or medial portion 18. Instead, the external surface forms a general oval configuration. Lateral surfaces 23 and 24 still extend through oppositely facing curves; however, top surface 21 and bottom surface 22 are smoothly contoured and blend into surfaces 23 and 24 providing the oval configuration as illustrated in FIG. 8. The upper surface 21 and lower surface 22 extend or project outwardly in the forward end portion 19 as compared to the position of both surfaces when extending through either the medial portion 18 or aft end portion 17. Notably, surfaces 23 and 24 form the opposite sides 25 and 26 of the tampon which extend in a rounded condition throughout the length of the tampon thereby occupying the lateral vaginal canals.

The tampon is made from the same material as existing tampons, namely a cotton/polyester material, but with an increase in volume which translates into a more absorbent capacity. The tampon main body can be produced utilizing a number or different techniques in order to obtain the configuration as depicted in the drawing. For example, the tampon main body may consist of a folded cotton/polyester material in a transverse oval shape which is flattened toward the center along its longitudinal axis 16 by a thread stitching 28 in a narrow inverted Y which extends in a loop that bridges together the two ends of the Y. Thus, stitching 28 (FIG. 1) may extend from the boundary between medial portion 18 and forward end portion 19 to a location approximately at the boundary of medial portion 18 and aft end portion 17 wherein the stitching branches out into two paths 29 and 30 securing the opposite ends 31 and 32 of loop 15. Alternatively, the tampon may be molded or foraged into the configuration illustrated in the drawing without utilizing stitching 28. In either design, the opposite ends of loop 15 are attached to the opposite sides of end 14 of the tampon main body.

Applicator sleeve 11 has a thin walled construction having an internal size larger than the exterior size of tampon 10 or plunger 12. The walls of sleeve 11 are very thin in order to allow for the sleeve containing the tampon to be folded along its longitudinal axis 33 (FIG. 5). Once tampon 10 has been inserted through opening 13 into sleeve 11, the sleeve with applicator is folded such as shown in FIG. 5 and then inserted in the vagina. Once inserted, the sleeve and tampon will recover its flattened shape when the pressure from the holding fingers is released. At this point, the tampon is ready to be extruded into the vaginal canal by holding plunger 12 against the tampon while pulling out the outer applicator sleeve. In order to favor easy insertion and to prevent excoriations of the vaginal wall, the applicator's leading or forward end 34 (FIG. 3) includes a pair of collapsed leaves 35 and 36 covering the forward opening 37. Leaves 35 and 36 (FIG. 7) have their proximal ends integrally attached to the main body or sleeve 11 with the outer or distal ends being unattached. Since the walls or leaves are thin, the opposite sleeves 35 and 36 will collapse as the sleeve with tampon is inserted. The external configuration of sleeve 11 is generally oval throughout the length of the sleeve; however, since the sleeve is thin walled, the sleeve will assume the general flattened figure 8 configuration as depicted in FIG. 4 prior to the insertion of the tampon. Likewise, once the tampon is inserted, the sleeve will conformingly fit around the tampon thereby assuming the external configuration of the tampon.

The forward end 19 of the tampon with sleeve is insertable most forwardly in the vagina with the loop or handle 15 being located at the opposite ends. By pulling on loop 15, the opposite ends 31 and 32 of the loop will pull the opposite sides of the tampon toward each other thereby facilitating the removal of the tampon. Notably, the width of the tampon extending in the direction of arrow 27 (FIG. 6) is substantially less than the length of the tampon extending along the longitudinal axis 16.

The present invention deals with a new and revolutionary design for a vaginal tampon which when inserted will fit almost perfectly to the female vaginal anatomy. This design will better allow for fulfilling the purpose of the tampon which is to absorb menstrual flow/blood and at the same time prevent leakage. Also, since the anatomical tampon fits its place of containment, removal will be remarkably easier and the chance for the user to forget that the tampon is in place is lessened. This characteristic will help prevent occurrences of Toxic Shock Syndrome. Since the possibilities of leakage are minimal, the user feels more free to continue carrying out daily activities. For example, the user may even become involved into water sports without the fear of embarrassment. This invention makes available a wider tampon surface for contact with the menstrual flow/blood which provides for more absorbency. This is particularly advantageous for use by women with heavy menstrual periods or uterine bleeding of other nature.

The preferred embodiment of the tampon is shown in FIGS. 9-13. Tampon 50 may be used with or without the applicator sleeve 11 and can be produced from the same material as tampon 10. The preferred embodiment of the tampon has a generally H-shaped cross section extending substantially the length of the tampon with one conical end being hollow to fittingly receive the uterine cervix. A channel is formed in the top surface and bottom surface of the main body of the tampon providing a pair of side ridges 51 and 52 arranged perpendicularly to a cross wall 53 in the general shape of a capital H. The outwardly facing surfaces of side ridges 51 and 52 are smooth and rounded forming a pair of outwardly facing convex surfaces. The top surface 54 of wall 53 is parallel to the bottom surface 55 of the wall. Surface 54 extends between and is perpendicularly arranged relative to the inwardly facing surfaces 56 and 57 respectively of side ridges 52 and 51. Likewise, bottom surface 55 extends between and is perpendicularly arranged to the inwardly facing surfaces 58 and 59 of respectively side ridges 52 and 51. Surfaces 54 and 55 extend frown one end 65 of the tampon main body to a pair of diverging surfaces 60 and 61, in turn, extending outwardly and blended into a pair of parallel surfaces 62 and 63 provided at the end portion adjacent end 64. Tampon 50 includes a longitudinal axis 75 extending the length of the tampon main body from end 64 to end 65 being positioned equidistant between side ridges 51 and 52.

End 64 is hollow having a conically shaped cavity 66. Cavity 66 has an interior closed end and extends inwardly from end 64 into the first end portion which is located between end 64 and the location where surfaces 60 and 61 diverge outwardly from flat surfaces 54 and 55. Walls 68 and 69 formed by cavity 66 are connected to the intermediate wall 53 with surfaces 60 and 61 located outwardly on walls 68 and 69. The cavity has an interior closed end but opens outwardly through end 64 forming a continuous thin wall 67 surrounding the cavity. Walls 68 and 69 include a cavity interior surface 75. The tampon of FIG. 14 is identical to the tampon of FIGS. 9-13 with the exception of the continuous wall 70 is oval in shape whereas wall 67 includes a pair of straight or flat edges 76 and 77 joined to the curved ends. Wall 70 surrounds cavity 71 which is conical in configuration.

Cavities 66 and 71 are designed to fittingly receive the uterine cervix upon full insertion of the tampon with wall 67 and wall 70 conformingly fitting around the cervix thereby anchoring the tampon to the carrier and preventing accidental dislodgement of the tampon upon movement of the carrier person. Wall 67 and wall 70 are flexible to conformingly receive the uterine cervix.

Cavity 66 is generally conical in configuration with wall 67 assuming the outward curved configuration of ridges 51 and 52. In between ridges 51 and 52, wall 67 is generally flat. In the alternate design shown in FIG. 14, wall 70 curves between ridges 51 and 52 providing a continuously curved configuration. Both cavities 66 and 71 open slightly to the left as viewed in FIG. 13 thereby racing upwardly when the tampon is inserted with surface 54 facing upwardly.

Tampon 50 may be provided with a string loop 15 and likewise may be positioned within applicator sleeve 11 in the same manner as described for tampon 10. In such a case, plunger 12 may be utilized with tampon 50. Alternatively, tampon 50 may be inserted and withdrawn without the necessity of the applicator sleeve or plunger. The H-shaped configuration of tampon 50 is designed to be essentially a mirror image of the cross section of the vagina. Thus, the H-shaped cross section of a tampon coupled with the cervix receiving hollow distal end of the tampon ensures the tampon will not be accidentally dislodged. The H-shaped cross section of the tampon main body is of uniform size along the longitudinal axis of the tampon from end 65 to the outwardly diverging surfaces 60 and 61.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

I claim:

1. An anatomical shaped vaginal tampon for insertion into a vagina comprising:
    a main body with length and having a first end and a second end and a longitudinal axis extending therebetween centrally along the length of said main body, said main body being of absorbent means operable to absorb menstrual flow. said main body having a pair of side ridges and a recessed intermediate wall extending therebetween, said first end including means that receives the cervix of the uterus and cooperatively with said intermediate wall and said side ridges complimentary first within the vagina limiting movement of said tampon.

2. The anatomical shaped vaginal tampon of claim 1 wherein:
    said means includes a cavity in said first end which opens outwardly through said first end, said main body includes a wall extending around said cavity which is flexible to conformingly receive said cervix.

3. The anatomical shaped vaginal tampon of claim 2 wherein:
    said first end is shaped in a generally oval configuration.

4. The anatomical shaped vaginal tampon of claim 2 and further comprising:
    an applicator sleeve having a thin walled construction defining a first hollow interior; and,
    stop means sized smaller than said applicator sleeve for insertion into said applicator sleeve, said stop means contactable against said main body for holding said main body stationary within the vagina as said applicator sleeve is withdrawn.

5. The anatomical shaped vaginal tampon of claim 2 wherein:
    said main body includes a first end portion with said first end located at said first end portion, said main body has a capital H cross section extending across said axis at said second end, said side ridges include outwardly facing smoothly curved surfaces whereas said intermediate wall includes a top flat surface and a bottom flat surface, said cross section is of uniform size from said second end to said first end portion whereat said top flat surface and said bottom flat surface diverge outwardly to said first end.

6. The anatomical shaped vaginal tampon of claim 5 wherein:
    said cavity has an interior closed end and extends inwardly from said first end into said first end portion to said closed end forming a pair of outwardly diverging walls connected to said intermediate wall, said top flat surface and said bottom flat surface diverge outwardly on said outwardly diverging walls.

7. The anatomical shaped vaginal tampon of claim 5 wherein:
    said cavity is conical in configuration.

8. A tampon for insertion into a vagina against the uterine cervix comprising:
    a main body of absorbent material having a length and a width substantially less than said length, said main body including a first end and a second end with cavity means at said first end thereof opening outwardly that receives the uterine cervix limiting movement of said main body relative to the vagina.

9. The tampon of claim 8 wherein:
    said cavity means includes a cavity and said main body includes a first end portion with said first end thereat, said main body includes an upwardly opening channel and a downwardly opening channel having an upper surface and a lower surface which extend from said second end to said first end portion whereat said upper surface and said lower surface diverge outwardly to said first end.

10. The tampon of claim 9 wherein:
    said main body includes a pair of side ridges and an intermediate wall extending therebetween, said side ridges include outwardly facing rounded surfaces whereas said intermediate wall has said upper surface and said lower surface thereon, said upper surface and said lower surface are flat and arranged perpendicularly to said side ridges.

11. The tampon of claim 10 wherein:
    said main body includes a pair of diverging walls at said first end portion connected to said intermediate wall, said diverging walls are connected together to surround said cavity and conformingly receive the uterine cervix.

12. A vaginal tampon comprising:
    a main body having length, a width substantially less than said length, and a longitudinal axis extending centrally along the length of said main body and being of absorbent material, said main body including a first end and a second end with cavity means at said first end thereof opening outwardly that receives the uterine cervix limiting movement of said main body relative to the vagina;
    an applicator sleeve having a thin walled construction defining a first hollow interior; and,
    stop means sized smaller than said applicator sleeve for insertion into said applicator sleeve, said stop means contactable against said main body holding said main body stationary within the vagina as said applicator sleeve is withdrawn.

* * * * *

UNITED STATES PATENT AND TRADEMARK OFFICE
CERTIFICATE OF CORRECTION

PATENT NO. : 5,370,633
DATED : December 6, 1994
INVENTOR(S) : Josue J. Villalta It is certified that error appears in the above-identified patent and that said Letters Patent is hereby corrected as shown below:

Column 2, line 56 delete "cereal" and insert --canal--.
Column 3, line 17 delete "PIG." and insert --FIG.--.
Column 4, line 5 delete "hereby" and insert --herein--.
Column 5, line 21 delete "foraged" and insert --formed--.
Column 7, line 8 delete "racing" and insert --facing--;
Column 7, line 45 delete "first" and insert --fits--.

Signed and Sealed this

Seventh Day of March, 1995

*Attest:*

BRUCE LEHMAN

*Attesting Officer*  *Commissioner of Patents and Trademarks*